(12) United States Patent
Ishiwata et al.

(10) Patent No.: US 6,787,653 B2
(45) Date of Patent: Sep. 7, 2004

(54) PREPARATION PROCESS OF BIPHENYLCARBOXYLIC ACID AMIDE DERIVATIVES

(75) Inventors: Hiroyuki Ishiwata, Ichikawa (JP); Seiichi Sato, Tokyo (JP); Mototsugu Kabeya, Higashimurayama (JP); Soichi Oda, Higashimurayama (JP)

(73) Assignee: Kowa Co., Ltd., Nagoya (JP)

( * ) Notice: Subject to any disclaimer, the term of this patent is extended or adjusted under 35 U.S.C. 154(b) by 39 days.

(21) Appl. No.: 10/162,602

(22) Filed: Jun. 6, 2002

(65) Prior Publication Data

US 2003/0232992 A1 Dec. 18, 2003

(51) Int. Cl.$^7$ ...................... C07D 211/26; C07D 213/36
(52) U.S. Cl. ........................................ 544/357
(58) Field of Search ........................................ 544/357

(56) References Cited

FOREIGN PATENT DOCUMENTS

WO    WO 99/42446    8/1999

*Primary Examiner*—Mukund J. Shah
*Assistant Examiner*—Hong Liu
(74) *Attorney, Agent, or Firm*—Oblon, Spivak, McClelland, Maier & Neustadt, P.C.

(57) ABSTRACT

A process for preparing a biphenylcarboxylic acid amide derivative represented by the following formula (1):

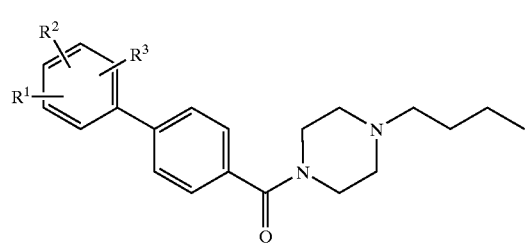

(1)

-continued

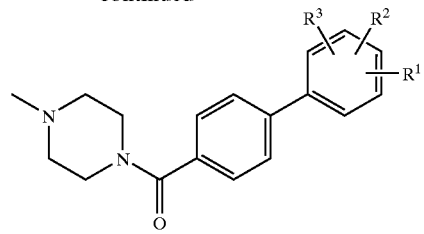

wherein, $R^1$, $R^2$ and $R^3$ each independently represents a hydrogen atom or a substituent, which comprises reacting, in the presence of a metal catalyst, a halogenobenzoic acid derivative represented by the following formula (2):

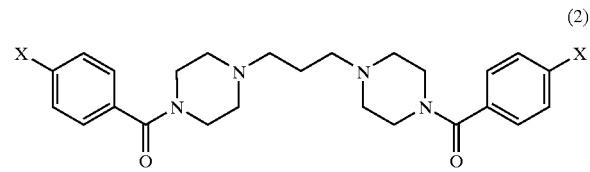

(2)

wherein, X represents a halogen atom with a compound represented by the following formula (3):

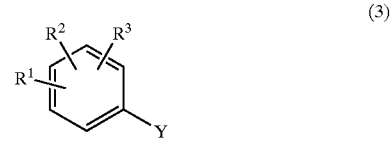

(3)

wherein, $R^1$, $R^2$ and $R^3$ have the same meanings as described above, and Y represents an leaving group having an element selected from the group consisting of boron, silicon, zinc, tin and magnesium; or salt thereof.

According to the present invention, biphenylcarboxylic acid amide derivatives of the formula (1) or salts thereof having excellent inhibitory activity against IgE antibody production can be prepared by the reduced number of steps, conveniently, at lower cost and in a high yield.

16 Claims, No Drawings

PREPARATION PROCESS OF BIPHENYLCARBOXYLIC ACID AMIDE DERIVATIVES

BACKGROUND OF THE INVENTION

1. Field of the Invention

The present invention relates to a preparation process for biphenylcarboxylic acid amide derivatives or salts thereof which have inhibitory activity against IgE antibody production and are, therefore, useful as a preventive or remedy for allergic immunological diseases.

2. Description of the Background

IgE antibody, which is a kind of immunoglobulin (Ig), is an allergen-specific molecule produced by an IgE antibody producing cell, which has been differentiated from a B cell, triggered by contact of an immunocyte with an allergen in vivo.

IgE antibody is produced in a target organ of an allergy and binds to a receptor on the surface of a mast cell, which is an important effector cell in an allergic reaction, or a basophil (sensitization). After sensitization, allergic chemical mediators such as histamine, leukotrienes, prostaglandins and PAF, and injuring enzymes such as tryptase are released from the mast cell, stimulated by an allergen which has invaded in the living body and reacted with the specific IgE antibody. Then, immediate allergic reactions such as increased vascular permeability, smooth muscle contraction and vasodilation are elicited. From the stimulated mast cell, cytokines such as IL-4, which directly activate other immune system cells, are also secreted. As a result, eosinophils, basophils and the like infiltrate into the tissue, and the allergic chemical mediators and tissue injuring proteins such as MBP, which are secreted by these inflammatory cells, induce a late-phase allergic reaction, thereby lingering the allergic symptom and making them serious.

From this, IgE antibody is considered a substance fundamentally taking part in allergic immunological diseases. A number of IgE antibody production inhibitors have been studied with a view to developing an antiallergic agent.

From such a viewpoint, the present inventors found that compounds having a diamide structure with aromatic rings at both ends of the molecule, particularly, 1,3-bis[4-[4-[(substituted)phenyl]benzoyl]-1-piperazinyl]propane which is a biphenylcarboxylic acid amide derivative represented by the following formula (1):

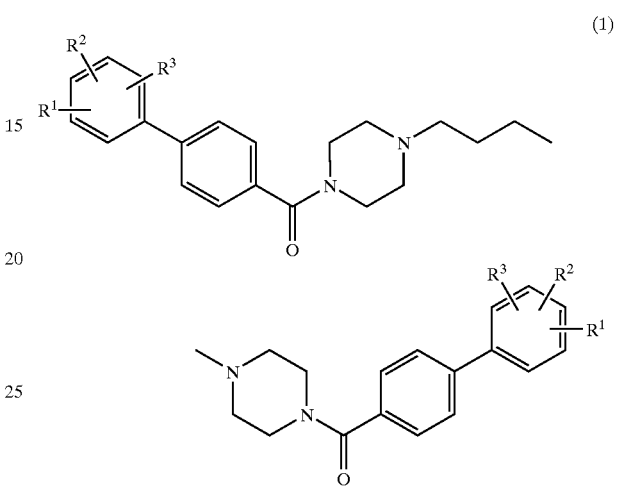

(1)

wherein, $R^1$, $R^2$ and $R^3$ each independently represents a hydrogen atom or a substituent) has excellent inhibitory activity against IgE antibody production and is useful as an anti-allergic, as described in international patent WO 99/42446.

The preparation process for the biphenylcarboxylic acid amide derivatives however comprises 6 steps as shown in the synthesis route described below. Thus, this route requires a large number of steps.

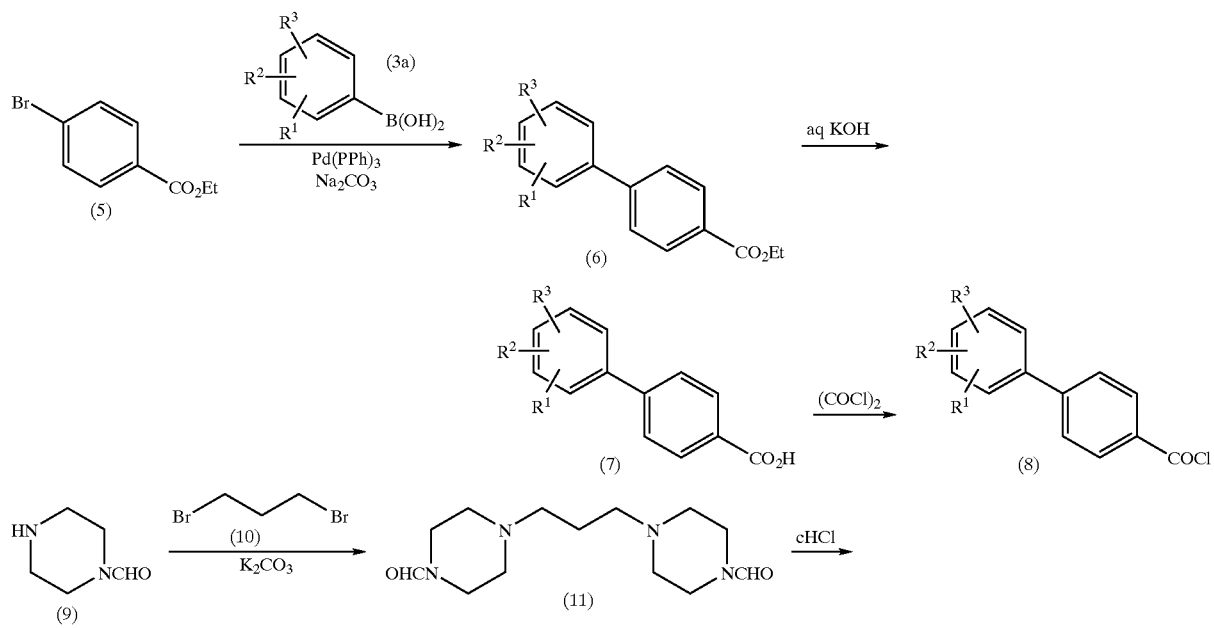

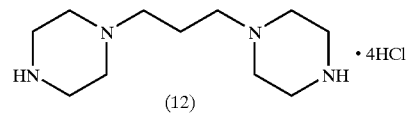

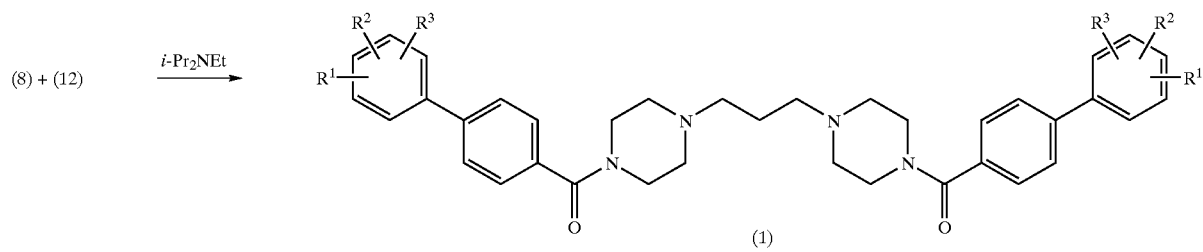

SUMMARY OF THE INVENTION

For forming a biphenylcarboxylic acid portion of the compound, a cross-coupling reaction (Suzuki reaction) using a (substituted)phenylboronic acid (3a) in the presence of a palladium catalyst is employed. The necessity of carrying out this reaction in the first step leads to an increase in the amount of expensive boronic acid (3a).

It is an object of the present invention to provide a process for preparing a biphenylcarboxylic acid amide derivative represented by the formula (1) or salt thereof conveniently by a reduced number of steps, at lower cost and in high yield.

With a view to developing a novel preparation process of a biphenylcarboxylic acid amide derivative represented by the formula (1) or salt thereof, the present inventors have carried out an extensive investigation. As a result, it has been found that the biphenylcarboxylic acid amide derivative represented by the formula (1) or salt thereof can be prepared by fewer steps in a high yield by reacting, in the presence of a metal catalyst, 1,3-bis[4-(4-halogenobenzoyl)-1-piperazinyl]propane, which is available from N-(4-halogenobenzoyl)piperazine and 1,3-di(leaving group)propane, with a (substituted)phenyl compound having a leaving group containing an element such as boron, thereby forming the biphenylcarboxylic acid portion of the compound in the final step, leading to the completion of the invention.

The present invention is represented by the following reaction scheme:

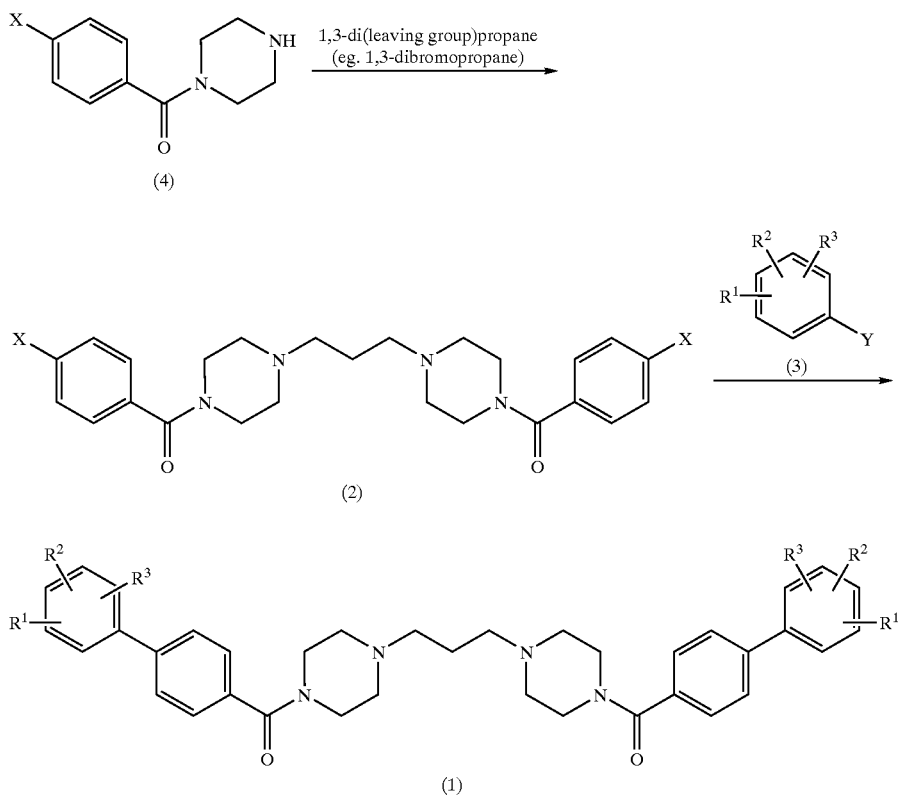

wherein X represents a halogen atom, Y represents an leaving group having an element selected from the group consisting of boron, silicon, zinc, tin and magnesium, and R$^1$, R$^2$ and R$^3$ each independently represents a hydrogen atom or a substituent.

In the present invention, there is thus provided a process for preparing a biphenylcarboxylic acid amide derivative represented by the formula (1) by reacting a halogenobenzoic acid derivative represented by the formula (2) with a compound represented by the formula (3) in the presence of a metal catalyst; or salt thereof.

Accordingly, the present invention provides a process for preparing a biphenylcarboxylic acid amide derivative represented by formula (1) or a salt thereof:

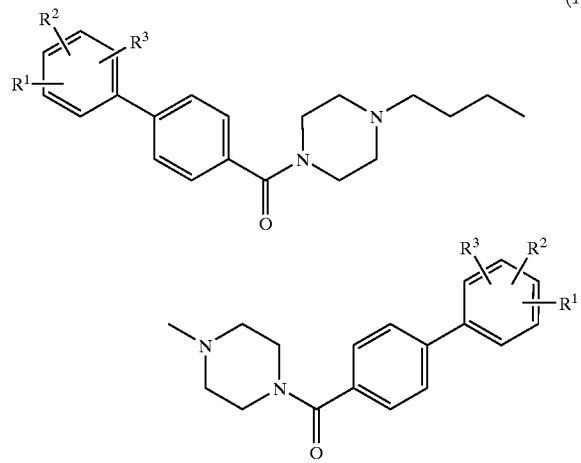

(1)

wherein

R$^1$, R$^2$ and R$^3$ each, independently, represent a hydrogen atom or a substituent selected from the group consisting of a hydroxyl group, halogen atoms, lower alkyl groups which may be substituted by 1 to 3 halogen atoms, lower alkoxy groups, amino group, mono(lower alkyl) amino groups, di(lower alkyl)amino groups, lower alkylthio groups, lower alkanoyl groups, and a formyl group, which comprises reacting, in the presence of a metal catalyst, a halogenobenzoic acid derivative represented by formula (2):

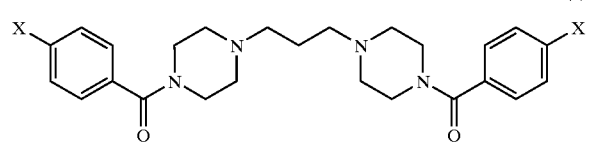

(2)

wherein

X represents a halogen atom, with a compound represented by formula (3):

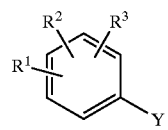

(3)

wherein

R$^1$, R$^2$ and R$^3$ have the same meanings as defined above, and

Y represents a leaving group having an element selected from the group consisting of boron, silicon, zinc, tin, and magnesium.

A more complete appreciation of the invention and many of the attendant advantages thereof will be readily obtained as the same becomes better understood by reference to the following description.

DETAILED DESCRIPTION OF THE INVENTION

In the present invention, it is preferred that the halogenobenzoic acid derivative (2) is prepared by reacting a compound represented by the formula (4) with a 1,3-di(leaving group)propane.

As each of R$^1$, R$^2$ and R$^3$ in the formulas (1) and (3), examples include hydrogen atom, hydroxyl group, halogen atoms, lower alkyl groups which may be substituted by 1 to 3 halogen atoms, lower alkoxy groups, amino group, mono (lower alkyl)amino groups, di(lower alkyl)amino groups, lower alkylthio groups, lower alkanoyl groups and formyl groups. Of these, preferred are hydrogen atom, lower alkyl groups which may be substituted by 1 to 3 halogen atoms, lower alkoxy groups, di(lower alkylamino) groups, lower alkylthio groups and lower alkanoyl groups, with lower alkoxy, lower alkanoyl and lower alkylthio groups being more preferred. A protecting group may be introduced as needed and after reaction, it may be removed. The term "lower" as used herein means that the group has 1 to 6 carbon atoms. This range includes all specific values.

As the lower alkyl groups, preferred are methyl, ethyl, n-propyl, isopropyl, n-butyl, isobutyl, s-butyl and t-butyl groups, of which methyl, ethyl, n-propyl and isopropyl groups are especially preferred.

Examples of the lower alkoxy groups include methoxy, ethoxy, n-propoxy, isopropoxy, n-butoxy, isobutoxy, s-butoxy and t-butoxy, with methoxy, ethoxy, n-propoxy and isopropoxy groups being preferred.

Examples of the lower alkanoyl groups include acetyl, propionyl, butyryl and isobutyryl groups, with acetyl and propionyl groups being preferred.

Examples of the lower alkylthio groups include methylthio, ethylthio, n-propylthio and isopropylthio groups.

Examples of the mono(lower alkyl)amino groups include methylamino, ethylamino, n-propylamino, and isopropylamino groups.

Examples of the di(lower alkyl)amino groups include dimethylamino, diethylamino, di(n-propyl)amino, and diisopropylamino groups.

Examples of the lower alkyl groups substituted by 1 to 3 halogen atoms include chloroethyl and trifluoromethyl.

Examples of the halogen atoms include chlorine, bromine, iodine and fluorine, with chlorine, bromine and fluorine being preferred.

As each of $R^1$, $R^2$ and $R^3$, especially preferred are $C_{1-6}$ alkoxy groups, $C_{2-6}$ alkanoyl groups and $C_{1-6}$ alkylthio groups.

It is preferred that $R^1$ and $R^3$ each represents a lower alkoxy group and $R^2$ represents a lower alkoxy, lower alkylthio or lower alkanoyl group.

$R^1$, $R^2$ and $R^3$ may be substituted at any position on the benzene ring, but they are preferably substituted at the 3-, 4- or 5-position respectively on the benzene ring. Described specifically, it is preferred that groups selected from $C_{1-6}$ alkoxy groups, $C_{2-6}$ alkanoyl groups and $C_{1-6}$ alkylthio groups are substituted at the 3-, 4- and 5-positions on the benzene ring.

There is no particular limitation imposed on the salt of a biphenylcarboxylic acid amide derivative (1) insofar as it is pharmaceutically acceptable. Examples of the salt include inorganic acid salts such as hydrochlorides, sulfates and nitrates and organic acid salts such as methanesulfonates, acetates, oxalates and citrates.

Preferred examples of the biphenylcarboxylic acid amide derivative (1) or salt thereof include 1,3-bis[4-[4-(3,4,5-trimethoxyphenyl)benzoyl]-1-piperazinyl]propane dihydrochloride, 1,3-bis[4-[4-(4-isopropoxy-3,5-dimethoxyphenyl)benzoyl]-1-piperazinyl]propane dimethanesulfonate, 1,3-bis[4-[4-(3,5-dimethoxy-4-methylthiophenyl)benzoyl]-1-piperazinyl]propane dihydrochloride, 1,3-bis[4-[4-(4-ethoxy-3,5-dimethoxyphenyl)benzoyl]-1-piperazinyl]propane dimethanesulfonate, 1,3-bis[4-[4-(4-acetyl-3,5-dimethoxyphenyl)benzoyl]-1-piperazinyl]propane dihydrochloride, and 1,3-bis[4-[4-(3,5-dimethoxy-4-propoxyphenyl) benzoyl]-1-piperazinyl]propane dihydrochloride.

The compound of the formula (4) which is a raw material compound of the invention process is available, for example, by reacting a 4-halogenobenzoyl chloride with piperazine in the presence of concentrated hydrochloric acid in accordance with the description in J. Med. Chem., 30, 49–57 (1987), incorporated herein by reference.

Per mole of the 4-halogenobenzoyl chloride, piperazine is used in an amount of 2 mole equivalents and concentrated hydrochloric acid is used in an amount of 2 mole equivalents. As the halogen atom represented by X in the formula (4), bromine is especially preferred.

The halogenobenzoic acid derivative (2) is available by condensation of the compound of the formula (4) and 1,3-di(leaving group)propane.

Examples of the 1,3-di(leaving group)propane include 1,3-dihalogenopropanes and compounds having equivalent reactivity with 1,3-dihalogenopropanes, such as bis(alkylsulfonyloxy)propanes. Of these, 1,3-dibromopropane is especially preferred.

The condensation reaction may be effected, if necessary, in a solvent such as methanol, ethanol, toluene, xylene, methylene chloride, dimethylformamide or dimethylsulfoxide, and if necessary, in the presence of an inorganic base such as sodium hydroxide, potassium hydroxide, sodium carbonate, sodium bicarbonate, potassium carbonate, potassium bicarbonate, sodium hydride or butyl lithium, or an organic base such as 1,8-diazabicyclo[4.3.0]undec-7-ene, pyridine or triethylamine. The reaction time and reaction temperature fall within ranges of 5 minutes to 100 hours and −20 to 100° C., respectively. They vary depending on the combination of the above-described raw materials. Particularly preferred is reaction of a halogenobenzoic acid derivative (2) with 1,3-dibromopropane in dimethylformamide in the presence of sodium carbonate as a base at 60 to 100° C. for 5 to 10 hours.

Coupling reaction of a halogenobenzoic acid derivative (2) with a compound of the formula (3) is conducted in a solvent in the presence of a metal catalyst (Metal-catalyzed Cross-coupling Reactions: Diederich, F.; Stang, P. J., Eds., Wiley-VHC: Weinheim, 1998, incorporated herein by reference.; Stanforth, S. P., Tetrahedron 1998, 54 263–303, incorporated herein by reference).

Examples of Y in the compound of the formula (3) include dihydroxyboron, (lower alkylenediolato)borons, di(lower alkoxy)borons, di(lower alkyl)borons, dihalogeno(lower alkyl)borons, dihalogeno(lower alkyl)silicons, halogenozincs, tri(lower alkyl)tins and halogenomagnesiums. Examples of the above-described lower alkylene group include $C_{2-6}$ alkylene groups. Of these, ethylene, propylene and tetramethylethylene groups are preferred. Examples of the lower alkoxy group include $C_{1-6}$ alkoxy groups, of which methoxy, ethoxy, n-propoxy and isopropoxy groups are preferred. Examples of the lower alkyl group include $C_{1-6}$ alkyl groups, of which methyl, ethyl, n-propyl and isopropyl groups are preferred. Examples of the halogen atom include fluorine, chlorine, bromine and iodine.

Dihydroxyboron and (pinacolato)boron are especially preferred as Y. (Miyaura, N; A. Suzuki, A. Chem. Rev. 1995, 95, 2457–2483, incorporated herein by reference).

The compound of the formula (3) can also be prepared from a corresponding halide or sulfonate ($-OSO_2C_qF_{2q+1}$ (q stands for 0 to 4)) in a reaction system (Miyaura, N. et al. Tetrahedron Lett. 1997, 38, 3447–3450, incorporated herein by reference; Giroux, A. et al. Tetrahedron Lett. 1997, 38, 3841–3844, incorporated herein by reference; Masuda, Y. et al. Org. Chem. 2000, 65, 164–168, incorporated herein by reference). Examples of the halogen of the halide include chlorine, bromine and iodine.

As the metal catalyst, preferred are palladium compounds such as tetrakis(triphenylphosphine)palladium(O), tris(bisbenzylideneacetone)dipalladium(O), palladium(II) acetate, palladium(II) chloride, dichlorobis(triphenylphosphine)palladium(II), dichloro[1,2-bis(diphenylphosphino)ethane]palladium(II), dichloro[1,4-bis(diphenylphosphino)butane]palladium(II), and dichloro[1,1'-bis(diphenylphosphino)ferrocene]palladium(II) and nickel compounds such as tetrakis(triphenylphosphine)nickel (O) and bis(acetylacetonato)nickel(II).

When Y of the formula (3) is a boron-containing leaving group, use of a palladium compound is particularly preferred.

As the solvent, use of benzene, toluene, xylene, diethyl ether, tetrahydrofuran, dimethoxyethane, dioxane, acetonitrile, dimethylformamide, N-methylpiperidone, methanol, ethanol or water is preferred, It is preferred to add a ligand and a base if necessary. Examples of the ligand include tri-butylphosphine, triphenylphosphine, tri(o-tolyl)phosphine, tri(2-furyl)phosphine, 2,2'-bis(diphenylphosphino)-1,1'-binaphthyl, 1,2-bis(diphenylphosphino)ethane, 1,3-bis(diphenylphosphino)propane, 1,4-bis(diphenylphosphino)butane and 1,1'-bis(diphenylphosphino)ferrocene, while examples of the base include sodium acetate, potassium carbonate, sodium carbonate, sodium bicarbonate, potassium phosphate, sodium hydroxide, potassium hydroxide, barium hydroxide, sodium methoxide, sodium ethoxide, cesium fluoride, tetxabutylammonium fluoride and triethylamine.

Reaction temperature and reaction time are 0 to 150° C. and 0.5 to 100 hours, respectively. When the leaving group of the compound of the formula (3) has boron and a palladium compound is used as a metal catalyst, reaction conditions at 0 to 80° C. for 2 to 15 hours are preferably employed.

The target compound can be isolated or purified from the reaction mixture, for example, by filtration, extraction, drying, concentration, recrystallization or various chromatographies.

The biphenylcarboxylic acid amide derivative (1) thus prepared can be converted into its acid addition salt in a conventional manner.

EXAMPLES

The present invention will hereinafter be described in detail by the following Examples. It should however be borne in mind that the present invention is not limited to or by these examples.

Preparation Example 1

1-(4-Bromobenzoyl)piperazine Hydrochloride

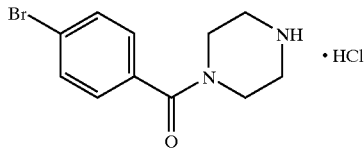

With ice cooling, 100 mL (1.2 mol) of concentrated hydrochloric acid was added in portions to a solution of 100.0 g (1.16 mol) of piperazine in water (200 mL)-methanol (300 ml) and the mixture was stirred for 30 minutes. To the resulting solution was added dropwise a solution of 127.4 g (0.58 mol) of 4-bromobenzoyl chloride in tetrahydrofuran (300 mL) over about 40 minutes, and the mixture was stirred for 30 minutes. The reaction mixture was concentrated under reduced pressure to remove tetrahydrofuran. To the residue was added water (2 L) and the mixture was stirred for 2 hours at 70° C. At this temperature, insoluble materials were filtered off and the residue was washed with hot water (20 mL). The filtrate and the washing were combined. After cooling to about 20° C., 74.4 g (1.86 mol) of sodium hydroxide was added and the mixture was extracted with ethyl acetate. The organic layer was washed with saturated saline, dried over anhydrous sodium sulfate and concentrated under reduced pressure. Isopropanol (400 mL) was added to the residue and the mixture was concentrated under reduced pressure. Isopropanol (1 L) was added again to the residue. The mixture was stirred at 50° C. to obtain a homogenous solution. Over about 20 minutes, 50 mL (0.60 mol) of concentrated hydrochloric acid was added dropwise to the resulting solution. After stirring for 10 minutes at 50° C., the mixture was cooled to room temperature, and stirred in an ice bath. The precipitates were collected by filtration and washed with isopropanol, whereby 140.1 g of 1-(4-bromobenzoyl)piperazine hydrochloride was obtained as colorless fine needles (yield: 79%).

mp: 262.5 to 263.0° C.

$^1$H NMR (CDCl$_3$) δ: 2.60–3.10 (br, 4H), 3.30–3.80 (br, 2H), 3.50–4.00 (br,2H), 7.28(d, J=8.4 Hz, 2H), 7.55(d, J=8.4 Hz, 2H).

Preparation Example 2

4-Isopropoxy-3,5-dimethoxyphenylboronic Acid

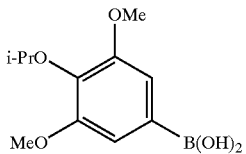

To a solution of 50.0 g of (0.170 mmol) of 1-iodo-3,4,5-trimethoxybenzene in methylene chloride (500 mL) was added 24.96 g (0.187 mmol) of aluminum chloride. The mixture was stirred at 60° C. for 6 hours. After cooling in an ice bath, ice (200 mL) and water (300 mL) were added and the resulting mixture was stirred. The reaction mixture was filtered through Celite and the aqueous layer of the filtrate was extracted with chloroform. The organic layers were combined, dried over anhydrous sodium sulfate and concentrated under reduced pressure. The residue was purified by chromatography on silica gel to yield crude crystals. The crude crystals were recrystallized from toluene-hexane, whereby 33.17 g of 4-hydroxy-l-iodo-3,5-dimethoxybenzene was obtained as a colorless crystalline powder (mp: 73.0 to 75.0° C., yield: 70%).

To a solution of 25.0 g (89.3 mmol) of 4-hydroxy-1-iodo-3,5-dimethoxybenzene in dimethylformamide (125 mL) were added 26.7 mL (267 mmol) of isopropyl iodide and 4.7 g (108 mmol) of a 55 wt. % sodium hydride dispersion in mineral oil. The reaction mixture was stirred at 50° C. for 2.5 hours. With ice cooling, water (125 mL) was added and the mixture was extracted with toluene-hexane (2:1). The organic layers were combined, dried over anhydrous sodium sulfate and concentrated under reduced pressure. The residue was purified by column chromatography on silica gel to yield crude crystals. The crude crystals were recrystallized from methanol, whereby 24.0 g of 1-iodo-4-isopropoxy-3,5-dimethoxybenzene was obtained as a colorless crystalline powder (mp: 56.0 to 57.0° C., yield: 83%).

Under nitrogen, 10 mL (159 mmol) of a 1.59 mol/L hexane solution of n-butyl lithium and a solution of 23.0 g (71.4 mmol) of 1-iodo-4-isopropoxy-3,5-dimethoxybenzene in anhydrous tetrahydrofuran (100 ml) were added dropwise to anhydrous tetrahydrofuran cooled in a dry ice-methanol bath, and the mixture was stirred for 30 minutes. After addition of 20 mL (87 mmol) of triisopropyl borate, the reaction mixture was stirred for 15 minutes and the dry ice-methanol bath was removed. With stirring, the reaction mixture was allowed to warm to room temperature over about 1.5 hours. After addition of water (4 mL, 200 mmol), the mixture was concentrated under reduced pressure and the residue was dissolved in a 1 mol/L aqueous sodium hydroxide solution (200 mL). After washing with heptane (20 mL) and chloroform (3×15 mL), the resulting solution was stirred in an ice bath, followed by dropwise addition of 35 mL (420 mmol) of concentrated hydrochloric acid. The mixture was stirred with ice cooling for 2.5 hours. The precipitates were collected by filtration, washed with 0.1 mol/L hydrochloric acid and water and air-dried overnight, whereby 16 g of crude crystals were obtained. A solution of crude crystals in tetrahydrofuran (50 mL) was dried over magnesium sulfate and then concentrated under reduced pressure to about 25 mL. The residue heated to about 80° C. was stirred, and heptane (15 mL) was added. After stirring at room temperature and then, in an ice bath, precipitates were collected by filtration and washed with tetrahydrofuran-heptane (1:10:3×7.5 mL), whereby 12.75 g of 4-isopropoxy-3,5-dimethoxyphenylboronic acid was obtained as a colorless crystalline powder (mp: 211.5° C. (decomposed), yield: 71%).

Preparation Example 3

3,5-Dimethoxy-4-methylthiophenylboronic Acid

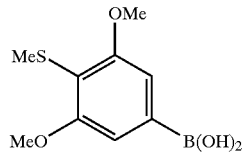

To a solution of 22.6 g (86.6 mmol) of 4-bromo-3,5-dimethoxybenzoic acid (*) in methylene chloride (400 mL) was added 1.5 mL (19.4 mmol) of dimethylformamide. With ice cooling, 13.0 g (102.0 mmol) of oxalyl chloride was added in portions and the mixture was stirred at room temperature for 1.5 hours. The reaction mixture was concentrated under reduced pressure, whereby crude crystals of 4-bromo-3,5-dimethoxybenzoyl chloride were obtained. To an ice-cold solution of 8.40 g (94.2 mmol) of 2-amino-2-methylpropanol in methylene chloride (100 mL), 16.6 mL (95.3 mmol) of N,N-diisopropylethylamine and a solution of crude 4-bromo-3,5-dimethoxybenzoyl in methylene chloride (200 mL) were added. After stirring at room temperature for 10 minutes, the reaction mixture was washed successively with water, 8.0 mol/L hydrochloric acid, a saturated aqueous solution of sodium bicarbonate and saturated saline, dried over anhydrous sodium sulfate and then concentrated under reduced pressure. To the residue was added 47.5 mL (651.0 mmol) of thionyl chloride and the mixture was stirred at room temperature for 10 minutes. Ice water and 600 mL (1500 mmol) of a 2.5 mol/L aqueous sodium hydroxide solution were added and the mixture was extracted with diethyl ether. The organic layer was washed with saturated saline, dried over anhydrous sodium sulfate and concentrated under reduced pressure. The residue was recrystallized from diethyl ether-hexane, whereby 20.9 g of 2-(4-bromo-3,5-dimethoxyphenyl)-4,4-dimethyl-2-oxazoline was obtained as colorless fine needles (mp: 172.5 to 174.5° C., yield: 77%). * Erdtman, H.; Leopold, B. Acta Chem. Scand. 1948, 2, 34–41 (Chem. Abstr. 1949, 43 1037i), incorporated herein by reference.

Under argon, 30.0 mL (0.199 mol) of N,N,N',N'-tetramethylethylenediamine and 134.0 mL (0.213 mol) of a 1.59 mol/L hexane solution of n-butyl lithium were added dropwise to a solution of 51.43 g (0.164 mol) of 2-(4-bromo-3,5-dimethoxyphenyl)-4,4-dimethyl-2-oxazoline in anhydrous tetrahydrofuran (1000 mL) stirred in a dry ice-methanol bath. After stirring for 10 minutes, 18.0 mL (0.2 mmol) of dimethyl disulfide was added and the mixture was stirred for 1 hour. Water was added to the reaction mixture and the organic solvents were removed under reduced pressure, then the residue was extracted with diethyl ether. The organic layer was washed with saturated saline, dried over anhydrous sodium sulfate and concentrated under reduced pressure. The residue was recrystallized from diethyl ether-hexane, whereby 34.8 g of 2-(4-methylthio-3,5-dimethoxyphenyl)-4,4-dimethyl-2-oxazoline was obtained as colorless fine needles (mp: 82.5 to 84.5° C., yield: 76%).

A solution of 34.70 g (0.123 mmol) of 2-(4-methylthio-3,5-dimethoxyphenyl)-4,4-dimethyl-2-oxazoline in 3.0 mol/L hydrochloric acid (450 mL) was stirred at 100° C. for 3 hours. The reaction mixture was extracted with methanol-chloroform (1:10). The organic layer was washed with saturated saline, dried over anhydrous sodium sulfate, and concentrated under reduced pressure. To a solution of the residue in methanol (50 mL) was added 100 mL (0.25 mol) of a 2.5 mol/L aqueous sodium hydroxide solution, and the mixture was stirred at 100° C. for 1 hour. With ice cooling, concentrated hydrochloric acid was added to make the reaction mixture acidic and the mixture was extracted with methanol-chloroform (1:10). The organic layer was washed with saturated saline, dried over anhydrous sodium sulfate and concentrated under reduced pressure, whereby 30.72 g of an oily material containing 3,5-dimethoxy-4-methylthiobenzoic acid was obtained.

To a solution of 30.72 g of the oily material obtained as above in t-butanol (459 mL) were added 14.2 g (140 mmol) of triethylamine and 39.1 g (142 mmol) of diphenylphosphoryl azide. After stirring at 100° C. for 2 hours, the reaction mixture was concentrated under reduced pressure. A solution of the residue in ethyl acetate was washed with a saturated aqueous solution of sodium bicarbonate and saturated saline, dried over anhydrous sodium sulfate and concentrated under reduced pressure. The residue was purified by column chromatography on silica gel, whereby 26.33 g of N-t-butoxycarbonyl-3,5-dimethoxy-4-methylthioaniline was obtained as colorless fine needles [mp: 123.5 to 125.5° C., yield: 71% from 2-(4-methylthio-3,5-dimethoxyphenyl)-4,4-dimethyl-2-oxazoline].

To a solution of 12.74 g (42.6 mmol) of N-t-butoxycarbonyl-3,5-dimethoxy-4-methylthioaniline in methanol (120 mL) was added 120 mL (480 mmol) of a 4.0 mol/L ethyl acetate solution of hydrogen chloride. The mixture was stirred at 50° C. for 1 hour and concentrated under reduced pressure. To the residue was added 70 mL (560 mmol) of a 8.0 mol/L aqueous sodium hydroxide solution and the mixture was extracted with chloroform. The organic layer was washed with saturated saline, dried over anhydrous sodium sulfate and concentrated under reduced pressure, whereby 8.5 g of an oily material containing 3,5-dimethoxy-4-methylthioaniline was obtained.

In water (186 mL) was suspended 8.5 g (about 43 mmol) of the oily material obtained as above. With ice cooling, 7.3 mL (88 mmol) of concentrated hydrochloric acid was added to the suspension to obtain a homogenous solution. With ice cooling, a solution of 3.15 g (45.7 mmol) of sodium nitrite in water (22 mL) was added dropwise to the resulting solution over about 10 minutes and the solution was stirred for 15 minutes. Then, a solution of 7.7 g (46 mmol) of potassium iodide in water (22 mL) was added. The reaction mixture was stirred at room temperature for 1 hour and at 50° C. for 15 minutes, then extracted with ethyl acetate. The organic layer was washed with saturated saline, dried over anhydrous sodium sulfate and concentrated under reduced pressure. The residue was purified by column chromatography on silica gel, whereby 8.9 g of 1-iodo-3,5-dimethoxy-4-methylthiobenzene was obtained as a brown crystalline powder (mp: 103.0 to 104.0° C., yield: 67% from N-t-butoxycarbonyl-3,5-dimethoxy-4-methylthioaniline).

By similar procedures applied in Preparation Example 2 for conversion of 1-iodo-4-isopxopoxy-3,5-dimethoxybenzene into 4-isopropoxy-3,5-dimethoxyphenylboronic acid, 4.1 g of 3,5-dimethoxy-4-methylthiophenylboronic acid was obtained as a colorless crystalline powder from 6.9 g (22,2 mmol) of 1-iodo-3,5-dimethoxy-4-methylthiobenzene (mp: 262.0 to 265.0° C., yield: 82%).

Preparation Example 4

4-Acetyl-3,5-dimethoxyphenyltrifluoromethanesulfonate

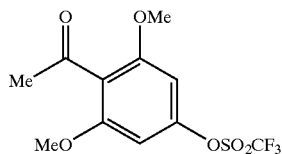

To a solution of 6.73 g (43.7 mmol) of 3,5-dimethoxyphenol in anhydrous dimethylformamide (50 mL) were added 5.95 g (87.4 mmol) of imidazole and 15.0 g (54.6 mmol) of t-butylchlorodiphenylsilane. The mixture was stirred at 50° C. for 4 hours. Water was added and the mixture was extracted with ethyl acetate-hexane (1:2). The organic layer was washed with water, dried over anhydrous sodium sulfate and concentrated under reduced pressure. The residue was purified by column chromatography on silica gel, whereby 16.14 g of 1-t-butyldiphenylsiloxy-3,5-dimethoxybenzene was obtained as a colorless crystalline powder (mp: 95.5 to 96.5° C., yield: 94%).

Under nitrogen, a solution of 7.85 g (22.0 mmol) of 1-t-butyldiphenylsiloxy-3,5-dimethoxybenzene in anhydrous diethyl ether (80 mL) was stirred in an ice bath and 16.6 mL (26.4 mmol) of a 1.59 mol/L hexane solution of n-butyl lithium was added. After stirring at 35° C. for 1.5 hours, the reaction mixture was stirred in an ice bath, and 2.34 mL (33.0 mmol) of acetyl chloride was added. After stirring at room temperature for 30 minutes, a saturated aqueous solution of ammonium chloride was added and the mixture was extracted with diethyl ether. The organic layer was washed with saturated saline, dried over anhydrous magnesium sulfate and concentrated under reduced pressure. The residue was purified by column chromatography on silica gel, whereby 2.07 g of 4-t-butyldiphenylsiloxy-2,6-dimethoxyacetophenone was obtained as a colorless oil (yield: 22%).

To a solution of 2.07 g (4.76 mmol) of 4-t-butyldiphenylsiloxy-2,6-dimethoxyacetaphenone in tetrahydrofuran (42 mL) was added 5.2 mL (5.2 mmol) of a 1.0 mol/L tetrahydrofuran solution of tetrabutylammonium fluoride. The reaction mixture was stirred at room temperature for 5 minutes, followed by concentration under reduced pressure. A solution of the residue in methylene chloride (63 mL) was stirred in a dry ice-methanol bath. After addition of 2.1 mL (12 mmol) of N,N-diisopropylethylamine, 1.2 mL (7.1 mmol) of trifluoromethanesulfonic anhydride was added dropwise. The reaction mixture was stirred for 30 minutes in a dry ice-methanol bath and the mixture was washed with 1.0 mol/L of hydrochloric acid and saturated saline, dried over anhydrous sodium sulfate and concentrated under reduced pressure. The residue was purified by column chromatography on silica gel, whereby 11.21 g of 4-acetyl-3,5-dimethoxyphenyltrifluoromethanesulfonate was obtained as a colorless oil (yield: 78%).

Example 1

1,3-Bis[4-[4-(3,4,5-trimethoxyphenyl)benzoyl]-1-piperazinyl]propane Dihydrochloride

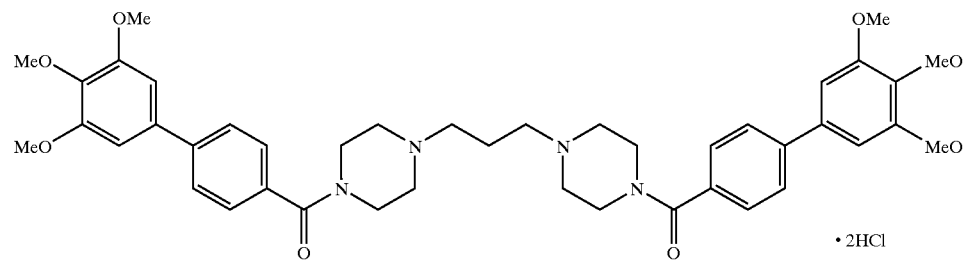

1-1:1,3-Bis[4-(4-bromobenzoyl)-1-piperazinyl] Propane

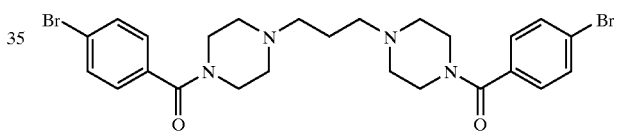

To a suspension of 66.7 g (0.218 mmol) of the 1-(4-bromobenzoyl)piperazine hydrochloride prepared in Preparation Example 1 in dimethylformamide (223 mL) were added 11.3 mL (98% purity, 0.109 mmol) of 1,3-dibromopropane and 33.5 g (0.316 mmol) of sodium carbonate. The mixture was stirred for 6 hours at 80° C. Water (670 mL) was added to the reaction mixture with stirring at 80° C. and the mixture was stirred for 0.5 hour at the same temperature and for 1.5 hours at 20° C. The precipitates were collected by filtration and washed with water (3×45 mL) to obtain crude crystals. A suspension of the crude crystals in water-isopropanol (7:3, 570 mL) was stirred for 2 hours at 85° C., for 0.5 hour at room temperature, and for 1 hour at 0° C. Precipitated crystals were collected by filtration and washed with water-isopropanol (5:1, 2×110 mL), whereby 60.0 g of 1,3-bis[4-(4-bromobenzoyl)-1-piperazinyl]propane was obtained as colorless fine needles (yield 95%) .mp: 170.0 to 173.0° C.

$^1$H NMR (DMSO-$d_6$, 120° C.) δ: 1.59 (quint, J=7.2 Hz, 2H), 2.32–2.45(m,12H), 3.44(br dd, J=5.0,5.0 Hz, 8H), 7.29(d, J=8.3 Hz, 4H), 7.58(d, J=8.3 Hz,4H).

1-2:1,3-Bis[4-[4-(3,4,5-trimethoxyphenyl)benzoyl]-1-piperazinyl]propane

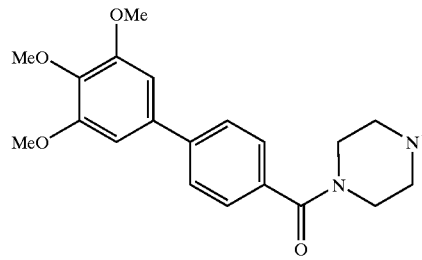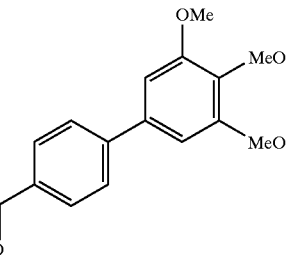

In toluene (200 mL)-methanol (50 mL) were dissolved 50.0 g (86.5 mmol) of 1,3-bis[4-(4-bromobenzoyl)-1-piperazinyl] propane and 42.16 g (199 mmol) of 3,4,5-trimethoxyphenylboronic acid. The mixture was degassed with nitrogen. A solution of 9.35 g (173 mmol) of sodium methoxide in methanol (150 mL) was added in portions, then a solution of 9.35 g (173 mmol) of sodium methoxide in methanol (150 mL) and a solution of 970 mg (4.32 mmol) of palladium(II) acetate in toluene (150 mL) were added dropwise simultaneously over about 1 hour. After stirring for 1 hour at room temperature, 9.2 g of activated carbon was added and the mixture was stirred under hydrogen for 3 hours at room temperature. Insoluble materials were filtered off by filtration through Celite and the residue was washed with methanol-toluene (1:1,3×75 mL). The filtrate and the washings were combined and concentrated under reduced pressure, then water-isopropanol (5:1, 750 mL) was added. After stirring for 30 minutes at room temperature, precipitates were collected by filtration and washed with water-isopropanol (5:1, 3×100 mL) to obtain 65.6 g of crude crystals. To a suspension of the crude crystals (65.6 g) in methanol-tetrahydrofuran (1:2, 350 mL) stirred at 70° C. was added 3.3 g of activated carbon, and the mixture was stirred for 1.5 hours. Insoluble materials were filtered off at the same temperature and the residue was washed with hot methanol-tetrahydrofuran (1:2, 2×130 mL). The filtrate and the washings were combined and stirred at 70° C. to obtain a homogeneous solution, then heptane (390 mL) was added over about 1 hour. The mixture was stirred for 30 minutes at room temperature and for 1 hour in an ice bath. Precipitates were collected by filtration and washed with tetrahydrofuran-heptane (1:5, 3×130 mL) to obtain 59.48 g of 1,3-bis[4-[4-(3,4,5-trimethoxyphenyl)benzoyl]-1-piperazinyl] propane as a colorless crystalline powder (yield: 92%).mp: 192.0 to 193.5° C.

$^1$H NMR (CDCl$_3$) δ: 1.71 (br quint, J=7.2 Hz, 2H), 2.43 (brt, J=7.2 Hz, 4H), 2.41–2.64(m, 8H), 3.35–4.05(m, 8H), 3.90(s, 6H), 3.93(s,12H), 6.77(s, 4H), 7.47 (d, J=8.3 Hz,4H), 7.59(d, J=8.3 Hz, 4H).

1-3:1,3-Bis[4-[4-(3,4,-trimethoxyphenyl)benzoyl]-1-piperazinyl] Propane Dihydrochloxide To a suspension of 20.0 g (26.6 mmol) of 1,3-bis[4-[4-(3,4,5-trimethoxyphenyl) benzoyl]-1-piperazinyl]propane in water (33.9 mL)-ethanol (267 mL) stirred at 70° C. was added 6.1 mL (73 mmol) of concentrated hydrochloric acid followed by ethanol (133 mL). The bath was removed and the resulting mixture (homogenous solution) was stirred for 30 minutes at room temperature and for 1 hour in an ice bath. Precipitates were collected by filtration and washed with ethanol (3×40 mL), whereby 21.42 g of 1,3-bis [4-[4-(3,4,5-trimethoxyphenyl)benzoyl]-1-piperazinyl] propane dihydrochloride was obtained as a colorless crystalline powder (yield: 98%).

mp: 265° C. (decomposed)

$^1$H NMR (DMSD-d$_6$, 120° C.) δ: 2.05–2.20 (m, 2H), 2.60–3.40 (m, 12H), 3.75(s, 6H), 3.72–3.84(m, 8H), 3.87(s, 12H), 6.92(s, 4H), 7.49 (d, J=8.0 Hz, 2H), 7.71(d, J=8.0 Hz, 2H).

* Ammonium NH$^+$ protons were not observed.

Example 2

1,3-Bis [4-[4-(4-isopropoxy-3,5-dimethoxyphenyl) benzoyl]-1-piperazinyl]propane Dimethanesulfonate

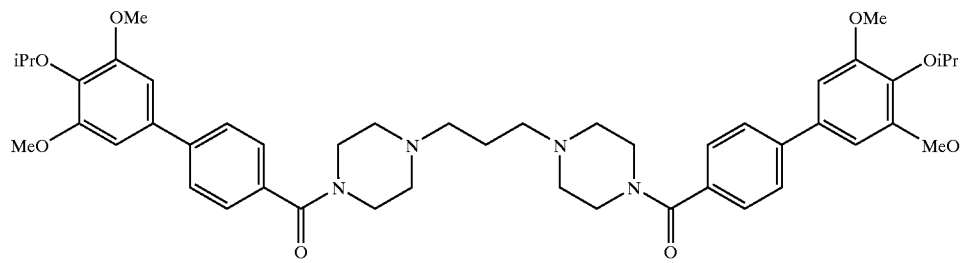

• 2MeSO$_3$H

Under nitrogen were added 2.40 mL (48 mmol) of a 2 mol/L aqueous sodium carbonate solution and 729.9 mg (0.632 mmol) of tetrakis(triphenylphosphine)palladium (0) to a solution of 4.50 g (7.79 mmol) of 1,3-bis[4-(4-bromobenzoyl)-1-piperazinyl]propane and 4.50 g (18.7 mmol) of 4-isopropoxy-3,5-dimethoxyphenylboronic acid in ethanol-toluene (15 mL –60 mL), and the mixture was stirred for 3 hours at 80° C. The reaction mixture was concentrated under reduced pressure to remove the organic solvents. Water (15 mL) was added to the residue and the mixture was extracted with chloroform (100 mL, 3×30 mL). The organic layers were combined, dried over anhydrous sodium sulfate, and concentrated under reduced pressure. The residue was purified by chromatography on silica gel to give 5.93 g of 1,3-bis[4-[4-(4-isopropoxy-3,5-dimethoxyphenyl)benzoyl]-1-piperazinyl]propane as a colorless oil (yield 94%).

A solution of 5.90 g (7.29 mmol) of 1,3-bis[4-[4-(4-isopropoxy-3,5-dimethoxyphenyl) benzoyl]-1-piperazinyl]propane in isopropanol (90 mL) was heated to 50° C. and a solution of 1.41 g (14.7 mmol) of methanesulfonic acid in isopropanol (30 mL) was added. t-Butyl methyl ether (30 mL) was added and the mixture was stirred for 5 minutes at 50° C., for 30 minutes at room temperature, then for 30 minutes in an ice bath. Precipitates were collected by filtration and washed with t-butyl methyl ether to afford 6.54 g of 1,3-bis[4-[4-(4-isopropoxy-3,5-dimethoxyphenyl) benzoyl]-1-piperazinyl]propane dimethanesulfonate as a colorless crystalline powder (yield: 90a). mp: 235.5° C. (decomposed).

$^1$H-NMR(CDCl$_3$) δ: 1.33(d, J=6.3 Hz,12H), 2.61–2.71(m, 2H), 2.80 (s, 6H), 2.84–3.10 (m, 4H), 3.0–5.0 (m, 4H), 3.37 (brt, J-7.6 Hz, 4H), 3.43–3.82(m, 8H), 3.90(s,12H), 4.42(qq, J=6.3, 6.3 Hz, 2H), 6.77(s, 4H), 7.47(d, J=8.3 Hz, 4H), 7.62(d, J=8.3 Hz, 4H), 10.5–11.5 (m, 2H).

Example 3

1,3-Bis[4-[4-(3,5-dimethoxy-4-methylthiophenyl) benzoyl]-1-piperazinyl]propane Dihydrochloride

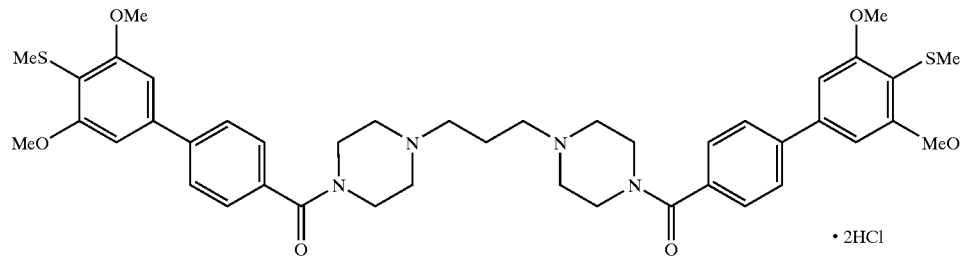

By similar procedures applied in Example 2, 136 mg of 1,3-bis[4-[4-(3,5-dimethoxy-4-methylthiophenyl)benzoyl]-1-piperazinyl]propane was obtained from 100.0 mg (0.173 mmol) of 1,3-bis[4-(4-bromobenzoyl)-1-piperazinyl]propane and 87.0 mg (0.381 mmol) of 3,5-dimethoxy-4-methylthiophenylboronic acid as a colorless oil (quantitative yield).

To a solution of 136 mg (0.173 mmol) of 1,3-bis[4-[4-(3,5-dimethoxy-4-methylthiophenyl)benzoyl]-1-piperazinyl]propane in chloroform (3 mL) stirred in an ice bath was added 0.11 mL (0.44 mmol) of a 4 mol/L ethyl acetate solution of hydrogen chloride, and the mixture was concentrated under reduced pressure. Methanol-diethyl ether was added and the precipitates were pulverized and collected by filtration to afford 105.0 mg of 1,3-bis[4-[4-(3, 5-dimethoxy-4-methylthiophenyl)benzoyl]-1-piperazinyl] propane dihydrochloride as a colorless amorphous powder (yield 71%).

$^1$H-NMR (DMSO-d$_6$) δ: 2.00–2.20 (m, 2H), 2.31(s, 6H), 2.5–3.5 (m,12H), 3.70–3.80(m, 8H), 3.91(s, 12H), 6.92(s, 4H), 7.52(d, J=8.1H z, 4H), 7.77 (d, J=8.1 Hz, 4H).

* Ammonium NH$^+$ protons were not observed.

Example 4

1,3-Bis[4-[4-(4-ethoxy-3,5-dimethoxyphenyl) benzoyl]-1-piperazinyl]propane Dimethanesulfonate

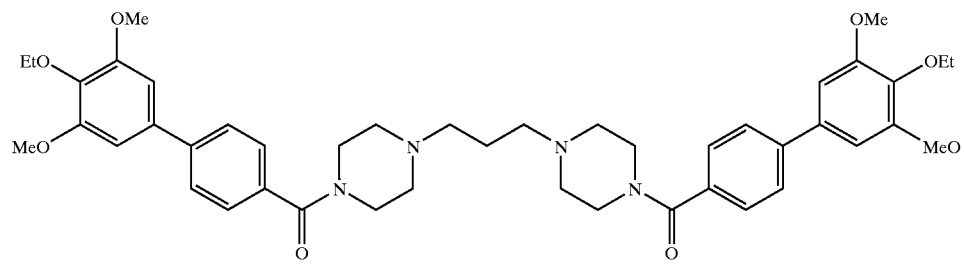

By similar procedures applied in Example 2, from 3.00 g (5.19 mmol) of 1,3-bis [4-(4-bromobenzoyl)-1-piperazinylapropane and 2.70 g (11.9 mmol) of 4-ethoxy-3,5-dimethoxyphenylboronic acid, 3.84 g of 1,3-bis[4-[4-(4-ethoxy-3,5-dimethoxyphenyl) benzoyl]-1-piperazinyl] propane was obtained as a colorless oil (yield 86%).

To a solution of 3.28 g (4.20 mmol) of 1,3-bis[4-[4-(4-ethoxy-3,5-dimethoxyphenyl) benzoyl]-1-piperazinyl] propane in methanol (10 mL) was added a solution of 808.2 mg (8.41 mmol) of methanesulfonic acid in methanol (5 mL). After addition of diethyl ether (15 mL), the mixture was stirred for 30 minutes at room temperature and for 30 minutes in an ice bath. Precipitates were collected by filtration and washed with methanol-diethyl ether (2:3) and diethyl ether to afford 3.29 g of 1,3-bis[4-[4-(4-ethoxy-3,5-dimethoxyphenyl)benzoyl]-1-piperazinyl]propane dimethanesulfonate as a colorless crystalline powder (yield: 80%). mp: 245.0° C. (decomposed)

$^1$H-NMR (CDCl$_3$) δ: 1.40(t, J=7.1 Hz, 6H), 2.62–2.74(m, 2H), 2.80 (s,6H), 2.88–3.06(m, 4H), 3.0–5.0(m, 4H), 3.36(br t, J=7, 1 Hz, 4H), 3.46–3.78 (m, 8H), 3.92 (s, 12H), 4.11 (q, J=7.1 Hz, 4H), 6.77 (s, 4H), 7.48 (d, J=8.5 Hz, 4H), 7.61(d, J=8.5 Hz, 4H).

* Ammonium NH$^+$ protons were not observed.

Example 5

1,3-Bis[4-[4-(4-acetyl-3,5-dimethoxyphenyl) benzoyl]-1-piperazinyl]propane Dihydrochloride Under argon, 105.0 mg (0.432 mmol) of bis(pinacolato)diboron, 16.0 mg (0.020 mmol) 5- of [1,1'-bis(diphenylphosphino)ferrocene]dichloropalladium(II) dichloromethane complex (1:1), and 117.0 mg (1.19 mmol) of potassium acetate were added to a solution of 130.0 mg (0.396 mmol) of the 4-acetyl-3,5-dimethoxyphenyl trifluoromethanesulfonate synthesized in Preparation Example 4 in dimethylformamide (5 mL), and the mixture was stirred for 1.5 hours at 80° C. To the reaction mixture were added 91.0 mg (0.158 mmol) of 1,3-bis[4-(4bromobenzoyl.)-1-piperazinyl]propane, 16 mg (0.020 mmol) of [1,1'-bis(diphenylphosphino)ferrocene]dichloropalladium(II) dichloromethane complex (1:1), and 1.0 mL (2.0 mmol) of a 2 mol/L aqueous sodium carbonate solution. After stirring for 2 hours at 80° C., water was added and the mixture was extracted with chloroform. The organic layer was washed with an aqueous saturated solution of sodium bicarbonate and saturated saline, dried over anhydrous sodium sulfate, and concentrated under reduced pressure. The residue was purified by chromatography on silica gel to give 115.9 mg of 1,3-bis [4-[4-(4-acetyl-3,5-dimethoxyphenyl)benzoyl]-1 piperazinyl]propane as a pale brown oil (yield: 94%).

To a solution of 78.0 mg (0.1 mmol) of 1,3-bis[4-[4-(4-acetyl-3,5-dimethoxyphenyl) benzoyl]-1-piperazinyl] propane in chloroform (3.0 mL) was added 0.063 mL (0.25 mmol) of a 4.0 mol/L ethyl acetate solution of hydrogen chloride, and the mixture was concentrated under reduced pressure. The residue was crystallized from chloroform-diethyl ether to afford 40.0 mg of 1,3-bis[4-[4-(4-acetyl-3,5-dimethoxyphenyl)benzoyl]-1-piperazinyl]propane dihydrochloride as a pale brown crystalline powder (yield: 47%). mp: 240.0° C. (decomposed)

$^1$H-NMR (CDCl$_3$) δ: 2.45–2.78 (m, 2H), 2.52 (s, 6H), 2.78–3.21 (m, 4H), 3.21–3.56 (m, 4H), 3.2–4.4 (m, 12H), 3.88 (s, 12H), 6.73 (s, 4H), 7.50 (br d, J=7.2 Hz, 4H), 7.63 (br d, J=7.2 Hz, 4H).

*Ammonium NH$^+$ protons were not observed.

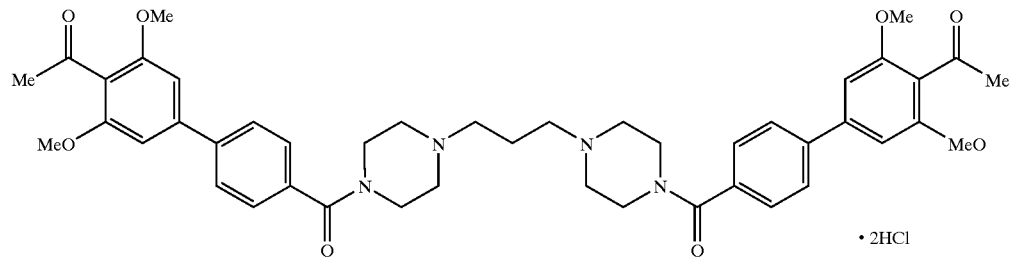

Example 6

1,3-Bis[4-[4-(3,5-dimethoxy-4-propoxyphenyl) benzoyl]-1-piperazinyl]propane Dihydrochloride

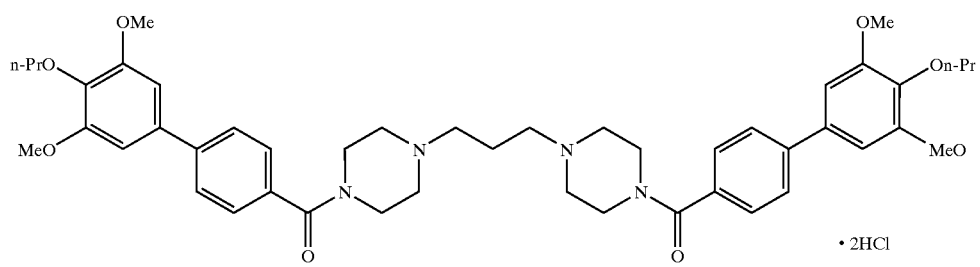

By similar procedures applied in Example 2, from 3.00 g (5.19 mmol) of 1,3-bis [4-(4-bromobenzoyl)-1-piperazinyl] propane and 3.00 g (12.5 mmol) of 3,5-dimethoxy-4-propoxyphenylboronic acid, 4.20 g of 1,3-bis[4[4-(3,5-dimethoxy-4-propoxyphenyl) benzoyl]-1-piperazinyl] propane was obtained as a colorless oil (quantitative yield).

To a solution of 4.2 g (5.19 mmol) of 1,3-bis[4-[4-(3,5-dimethoxy-4-propoxyphenyl) benzoyl]-1-piperazinyl] propane in methanol (30 mL) stirred in an ice bath, was added 3.2 mL (13 mmol) of a 4.0 mol/L ethyl acetate solution of hydrogen chloride, and the mixture was concentrated under reduced pressure. Methanol (50 mL) was added and the mixture was concentrated under reduced pressure again. A suspension of the residue in methanol-chloroform (10:1, 44 mL) was stirred at 40° C. to give a homogeneous solution. Diethyl ether (10 mL) was added to the solution and the mixture was stirred at room temperature and at 0° C. Precipitates were collected by filtration and washed successively with methanol-diethyl ether (2:3) and diethyl ether to afford 3.92 g of 1,3-bis[4-[4-(3,5-dimethoxy-4-propoxyphenyl) benzoyl)-1-piperazinyl]propane dihydrochloride as a colorless crystalline powder (yield: 86%).

mp: 266.0° C. (decomposed)

$^1$H-NMR (CDCl$_3$) δ: 1.03 (t, J=7.2 Hz, 6H), 1.80 (sext, J=7.2 Hz, 4H), 2.60–2.71(m, 2H), 2.92–3.10(m, 4H), 3.5–5.0(m, 8H), 3.36–3.50 (m, 4H), 3.62–3.76(m, 4H), 3.91(s, 12H), 3.98(t, J=7.2 Hz, 4H), 6.77 (s, 4H), 7.48 (d, J=8.3 Hz, 4H), 7.62 (d, J=8.3 Hz, 4H).

*Ammonium NH$^+$ protons were not observed.

Test 1

Evaluation of Inhibitory Activity Against IgE Antibody Production

After the spleen was enucleated from a mouse (Balb/C, male, aged 8 weeks) and shredded in 0.3 wt. % BSA/HBSS, single cells were obtained using a 200-mesh screen. The single cells were then hemolyzed by a 0.75 wt. % ammonium chloride·17 mmol/L Tris solution and a splenocyte suspension (1×10$^7$/mL) was prepared using RPMI 1640 medium/25 mmol/L HEPES/0.3 wt. % BSA. After the suspension was reacted with a rat anti-mouse Thy-1,2 monoclonal antibody (product of Cedarlane Co.) at 4° C. for 1 hour, the reaction mixture was centrifuged and the sediment cells were suspended again (1×10$^7$/mL, RPMI/HEPES/BSA). After the suspension-was reacted with a low-cytotoxic rabbit complement (product of Cedarlane Co.) at 37° C. for 1 hour, killed cells were removed by specific gravity centrifugation using lympholyte M (product of Cedarlane Co.) to obtain a B cell fraction as viable cells.

After culturing B cells (105/0.2 mL/well) for one day together with LPS (E. coli 026:B6, product of DIFCO Co.) on a 96-well plate, mouse IL-4 (product of Genzyme Co.) was added. The mixture was cultured for further 7 days. Each test compound was added on the first day of the culture. After culturing, the amount of IgE antibody in a culture supernatant was assayed by ELISA, and the inhibitory activity of the test compound against production of an IgE antibody was calculated. The inhibitory activity (IC$_{50}$) is shown in Table 1.

TABLE 1

| Test compound | IC$_{50}$ (:M) |
|---|---|
| Example 1 | 0.1 |
| Example 2 | 0.2 |
| Example 3 | 0.08 |
| Example 4 | 0.4 |
| Example 5 | 0.6 |
| Example 6 | 0.3 |

INDUSTRIAL APPLICABILITY

According to the present invention, biphenylcarboxylic acid amide derivatives represented by the formula (1) or salts thereof which have excellent inhibitory activity against IgE antibody production and are therefore useful as a medicament can be prepared by the reduced number of steps, conveniently, at lower cost and in a high yield.

What is claimed is:

1. A process for preparing compound represented by formula (1) or a salt thereof:

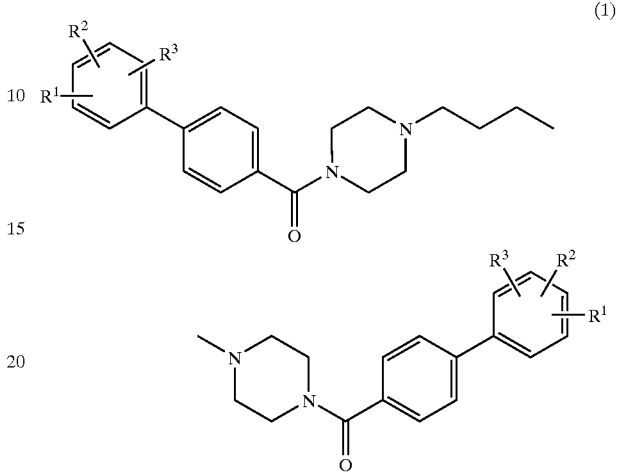

wherein
R$^1$, R$^2$ and R$^3$ each, independently, represent a hydrogen atom or a substituent selected from the group consisting of a hydroxyl group, halogen atoms, lower alkyl groups which may be substituted by 1 to 3 halogen atoms, lower alkoxy groups, amino group, mono(lower alkyl)amino groups, di(lower alkyl) amino groups, lower alkylthio groups, lower alkanoyl groups, and a formyl group, which comprises reacting, in the presence of a metal catalyst, a halogenobenzoic acid compound represented by formula (2):

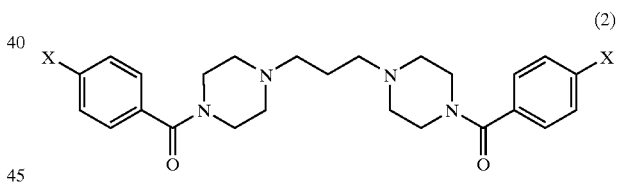

wherein
X represents a halogen atom,
with a compound represented by formula (3):

wherein
R$^1$, R$^2$ and R$^3$ have the same meanings as defined above, and
Y represents a leaving group having an element selected from the group consisting of boron, silicon, zinc, tin, and magnesium.

2. The process of claim 1, wherein Y is selected from the group consisting of dihydroxyboron, (lower alkylenediolate) borons, di(lower alkoxy)borons, di(lower alkyl)borons, dihalogeno(lower alkyl)borons, dihalogeno(lower alkyl)

silicons, halogenozincs, tri(lower alkyl)tins, and halogenomagnesiums.

3. The process of claim 1, wherein the compound of the formula (2) has been prepared by reacting a compound represented by formula (4)

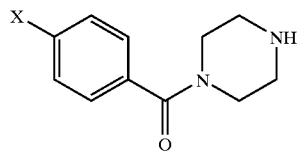

(4)

wherein x has the same meaning as defined in claim 1, with a 1,3-di(leaving group)propane.

4. The process of claim 1, wherein the compound of formula 1 has $R^1$, $R^2$ and $R^3$ substituted at the 3-, 4- and 5-positions respectively on the benzene ring.

5. The process of claim 1, wherein $R^1$ and $R^3$ each is a lower alkoxy group and $R^2$ is a lower alkoxy group, a lower alkylthio group or a lower alkanoyl group.

6. The process of claim 1, wherein $R^1$, $R^2$, and $R^3$ are, independently, selected from the group consisting of hydrogen, lower alkyl groups which may be substituted by 1 to 3 halogen atoms, lower alkoxy groups, di(lower alkylamino) groups, lower alkylthio groups, and lower alkanoyl groups.

7. The process of claim 1, wherein $R^1$, $R^2$, and $R^3$ are, independently, selected from the group consisting of $C_{1-6}$ alkoxy groups, $C_{2-6}$ alkanoyl groups, and $C_{1-6}$ alkylthio groups.

8. The process of claim 1, wherein the metal catalyst is a palladium compound.

9. The process of claim 1, wherein the metal catalyst is a nickel compound.

10. The process of claim 1, wherein the metal catalyst is selected from the group consisting of tetrakis(triphenylphosphine)palladium(O), tris(bisbenzylideneacetone)dipalladium(O), palladium(II) acetate, palladium(II) chloride, dichlorobis(triphenylphosphine)palladium(II), dichloro[1,2-bis(diphenylphosphino)ethane]palladium(II), dichloro[1,4-bis(diphenylphosphino)butane]palladium(II), dichloro[1,1'-bis(diphenylphosphino)ferrocene]palladium(II), tetrakis(triphenylphosphine) nickel (O), and bis(acetylacetonato)nickel(II).

11. The process of claim 1, wherein X is bromine.

12. The process of claim 1, wherein Y is dihydroxyboron or (pinacolato)boron.

13. The process of claim 1, wherein Y is a boron containing leaving group and the metal catalyst is a palladium compound.

14. The process of claim 1, wherein the compound represented by formula (1) is 1,3-bis[4-[4-(3,4,5-trimethoxyphenyl)benzoyl]-1-piperazinyl]propane dihydrochloride, 1,3-bis[4-[4-(4-isopropoxy-3,5-dimethoxyphenyl)benzoyl]-1-piperazinyl]propane dimethanesulfonate, 1,3-bis[4-[4-(3,5-dimethoxy-4-methylthiophenyl)benzoyl]-1-piperazinyl]propane dihydrochloride, 1,3-bis[4-[4-(4-ethoxy-3,5-dimethoxyphenyl)benzoyl]-1-piperazinyl]propane dimethanesulfonate, 1,3-bis[4-[4-(4-acetyl-3,5-dimethoxyphenyl)benzoyl]-1-piperazinyl]propane dihydrochloride, or 1,3-bis[4-[4-(3,5-dimethoxy-4-propoxyphenyl)benzoyl]-1-piperazinyl]propane dihydrochloride.

15. The process of claim 1, wherein (2) and (3) are reacted at a temperature of 0 to 150° C. for a period of 0.5 to 100 hours.

16. The process of claim 1, wherein Y has a boron atom, the metal catalyst is a palladium compound, and (2) and (3) are reacted at a temperature of 0 to 80° C. for a period of 2 to 15 hours.

* * * * *